Feb. 16, 1971 J. L. THOMPSON Plant Pat. 3,028
CRABAPPLE TREE
Filed Jan. 27, 1969
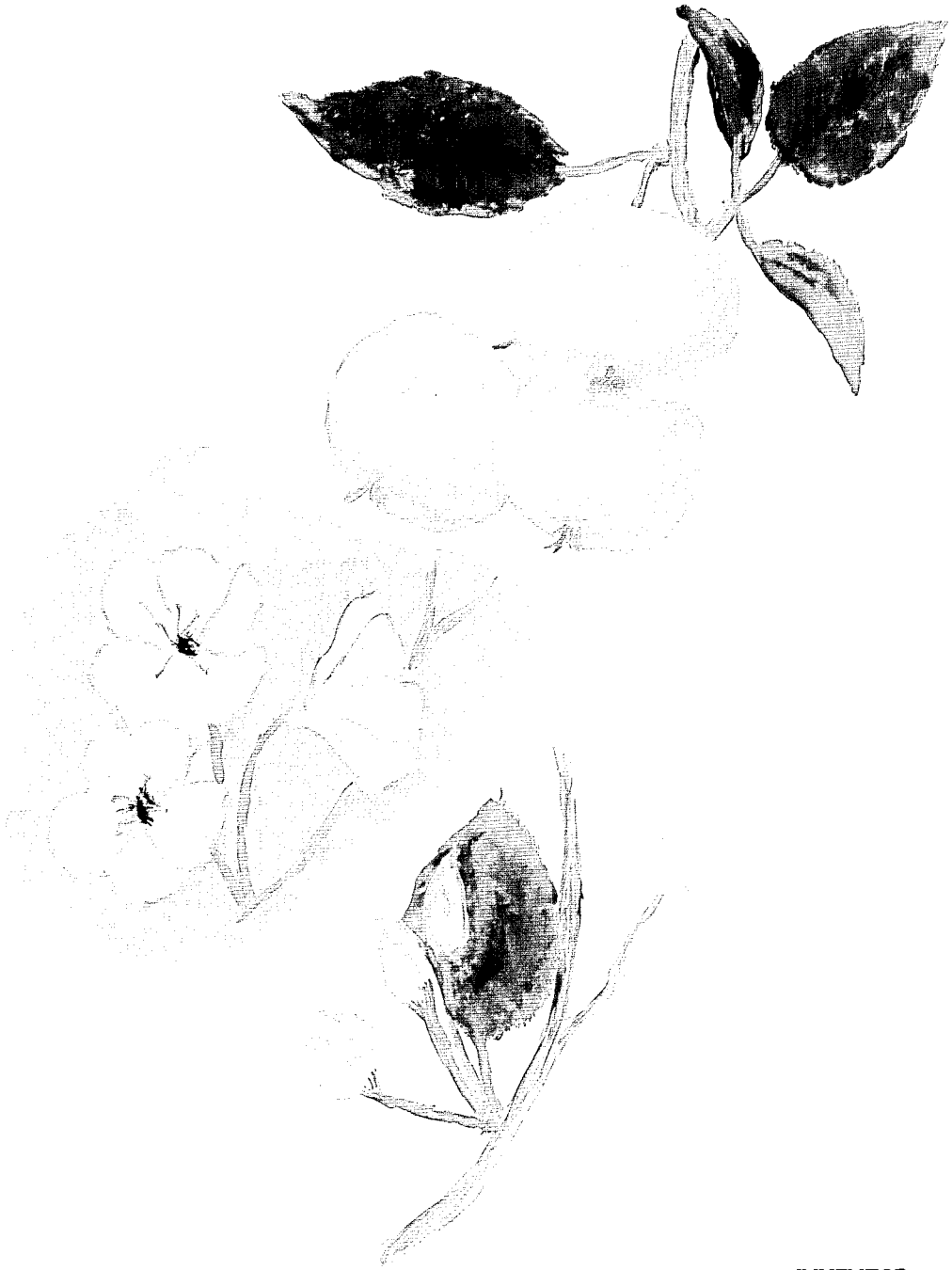
INVENTOR.
BY John Lee Thompson United States Patent Office Plant Pat. 3,028
Patented Feb. 16, 1971

3,028
CRABAPPLE TREE

Johnn Lee Thompson, Rte. 1, Maryville, Mo. 64468
Filed Jan. 27, 1969, Ser. No. 794,429
Int. Cl. A01h 5/03
U.S. Cl. Plt.—34 1 Claim The new hybrid is believed to be a cross between Golden Delicious, a variety of *Malus sylvestris* or *Malus pumila*—depending upon the horticultural encyclopedia handbook consulted, and Dolgo crab, a crabapple hybrid of *Malus sylvestris* or *Malus baccata*—again depending upon the handbook consulted. It has the coloring of the Golden Delicious apple and the crab-like characteristics of the Dolgo but is larger in size and slightly different in shape than the Dolgo crab. The cultivar name of my new variety is "Golden Wax."

The most striking feature of the fruits is their color. Subglobose in shape and occurring in an indefinite number, generally profuse, the yellow pomes are generally one inch to one inch and one-half in diameter (approximately two and one-half to three and one-half centimeters in diameter) or occasionally larger depending upon the growing season, the amount of rainfall, and the number of fruits that have set on. The calyx of the fruits is protuberant, pubescent, and persistent. Depending upon the degree of ripeness, fruits are generally Aureolin in hue; that is, the color most approximates this hue found on plate 10, swatch L2, in the following color authority: A Dictionary of Color by A. Maerz and M. Rea Paul, 2nd ed., New York: McGraw-Hill Book Company, Inc., 1950. Variances can be found in the coloring of a single fruit or in several fruits of the same cluster, ranging generally from Red Yellow, plate 10, swatch I1 of the same color authority; Sulphur Yellow, plate 10, swatch J1; through Aureolin—already mentioned; to Sunflower Dandelion, plate 9, swatch K4. When a "blush" seemed to be present, these hues seemed discernible: Plate 10, swatch I3, hue unnamed, to Light Chrome Yellow, plate 10, swatch I4. (All color names and swatches are from the same color source previously cited.)

The fruit has a wax-like appearance as it approaches ripeness indicating a high amount of pectin. There is some stippling of an indeterminate brown color on the Aureolin ground; the dots are about the size of a fine point. The fruit becomes mealy in texture as it ripens and loses its "bitter, green crab" taste. The flesh or pulp of the fruit is white.

Blossoms are profuse, one to two inches across, not at all distinctive from other varieties of *Malus sylvestris* found in an orchard on the same farm, varieties such as Golden Delicious, Jonathan, Red Delicious, Anoka, Winesap, or Yellow Transparent. They are pink in the bud becoming white when fully open and appear with the foilage or just before it. The new hybrid reaches peak bloom at about the same time as the Jonathan variety, blooming time dependent upon the season, and the fruit is usually ripe at its location in Maryville, Mo., about mid-August.

Its height at full growth or maturity is still indeterminate.

Branchlets are more or less woolly, at least toward the tip; buds are grayish, hairy at the tip and blunt. Terminal buds are present, much larger than the lateral; stipule scars are lacking, and there are three bundle scars. The bark is dark-grayish brown and smooth through flakiness has now appeared near the base of the trunk. Unless there is fruit on the tree, there seems little difference between this tree and some twenty otther varieties of orchard apples on the same farm except possibly for occasional spinescent branches close to the lower trunk.

The leaves of the new hybrid are pubescent to glabrate and are glabrous at maturity. There are tangled hairs especially along veins on the lower surface. Leaves are scarcely woolly after fully opening but pubescent beneath and glabrate above. The leaves' lengths range from one and one-half to two inches long (three and one-half centimeters to approximately five centimeters), and the leaves are serrulate. At the base, leaves are rounded or cordate. Generally, the leaves are ovate to elliptic in shape but a few leaves are lance-ovate. The branchlets are alternately leafed, and the leaves have six to nine pairs of veins. The petioles have a whitish pubescence and are slender, glabrous underneath and villose on the upper surface of the petiole. The petioles are generally from one inch to one and one-half inches in length (two and one-half centimeters to approximately four centimeters).

The pedicels are also generally from one inch to one and one-half inches in length (two and one-half centimeters to approximately four centimeters) and are slender and tenacious. The fruits for the most part do not form an abscission layer in ripening but are persistent, becoming putrescent and brown on the tree.

The horticulture department at the University of Missouri at Columbia, whom samples were mailed to, expressed the opinion that the tree's probable chief value would be for ornamental purposes and/or for making jellies.

The hybrid tree is located on the John W. Thompson farm, three miles south of Maryville, Mo., in the northwest part of the state. It is located sixty yards east of the U.S. Highway 71 right-of-way line in a plot of ground that has been a vegetable garden since 1954. Previously the ground had been a pasture until the farmhouse was moved in 1953 because of a widening of the federal highway, at which time the land was plowed under to become a family vegetable garden. The tree is now six years old and is growing in an asparagus bed. It assumedly grew from Golden Delicious seeds planted by the inventor in the asparagus bed where they would be relatively undisturbed. More specifically, the tree is twenty-eight yards due east of the Thompson farm house. It is eight yards west from an electric light pole that carries the wires to a farm well and is the only apple tree presently growing in this garden plot of about one-half acre. The tree was definitely not found in an uncultivated state.

One of the parents of the hybrid, presumably because the seed was taken from the parings of pomes of this three, was a Golden Delicious, now dead, which was some fifty yards away from the Dolgo Crab, which is assumedly crossed with. The seeds were planted next to a row of asparagus plants. The other assumed parent of the hybrid, a Dolgo crab, still living, supposedly has given the fruit of the new tree those characteristics which are crab-like. At the time of the planting of the seeds—this hybrid was the only tree which grew—there were no other crab trees on the farm although some ornamental crabs have been planted in the last four years. This opinion of the new crab's parentage is also shared by Aubrey D. Hibbard, professor of horticulture of the Horticulture Department of the University of Missouri at Columbia; Professor Hibbard was mailed a sample of the pomes. He stated in a letter dated Aug. 11, 1966: "This [yellow crab] has all the ear marks of being a cross between the Dolgo, your red crab, and a Yellow Delicious apple. The crab showed many bruised spots which is quite characteristic of Golden Delicious."

Thus far the tree has been asexually reproduced only in the Midwest. Fifty bud stick cuttings have been sent to Wayside Gardens in Mentor, Ohio, for grafting, evaluation, and testing, and three bud sticks were mailed to the Missouri State Fruit Experimental Farm, Mountain Grove, Mo. Successful branch graftings have also been made by the applicant in the spring of 1968 onto a young Jon-A-Red apple tree, an improved form of Jonathan apple.

I claim:

1. A new and distinct variety of crabapple substantially as shown and described, characterized by its yellow fruit color and profuse blooming habit.

No references cited.

ROBERT E. BAGWILL, Primary Examiner